United States Patent [19]
Franke et al.

[11] 3,939,274
[45] Feb. 17, 1976

[54] PHENOXYPHENYLALKANOIC ACID ESTER INSECTICIDES

[75] Inventors: Albrecht Franke, Ludwigshafen, Germany; Walter Traber, Riehen, Switzerland

[73] Assignee: Ciba-Geigy Corporation, Ardsley, N.Y.

[22] Filed: Apr. 3, 1974

[21] Appl. No.: 457,524

Related U.S. Application Data
[62] Division of Ser. No. 252,783, May 12, 1972, Pat. No. 3,824,274.

[30] Foreign Application Priority Data
May 15, 1971 Switzerland.......................... 7205/71
Apr. 6, 1972 Switzerland.......................... 5087/72

[52] U.S. Cl. ................ 424/308; 424/304; 424/309; 424/324
[51] Int. Cl.² ........................................ A01N 9/24
[58] Field of Search............................ 424/308, 309

[56] References Cited
UNITED STATES PATENTS
3,600,437   8/1971   Marshall .......................... 260/473 R
3,739,015   6/1973   Wattanabe et al.............. 260/473 R

*Primary Examiner*—V. D. Turner
*Attorney, Agent, or Firm*—Harry Falber

[57] ABSTRACT

Compounds of the formula

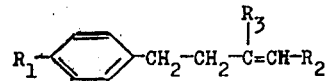

wherein $R_1$ represents a phenyl, phenoxy, phenylthio or cyclohexyl radical which is optionally substituted by halogen, nitro, alkyl and/or alkoxy, or a phenyl or cyclohexyl radical which is bonded via an alkylene, alkyleneoxy or alkylenethio bridge member, $R_2$ represents cyano, carbamoyl, an alkoxycarbonyl, alkenyloxycarbonyl, alkinyloxycarbonyl, alkylcarbamoyl or dialkylcarbamoyl radical and $R_3$ represents hydrogen or alkyl, their manufacture and agents for influencing the development of insects are disclosed.

13 Claims, No Drawings

PHENOXYPHENYLALKANOIC ACID ESTER INSECTICIDES

This is a division of application Ser. No. 252,783, filed on May 12, 1972, now U.S. Pat. No. 3,824,274.

The present invention relates to new 4-phenyl-2-methyl-1-butene-1-carboxylic acid derivatives, their manufacture and their use in influencing the development of insects.

The new compounds correspond to the formula

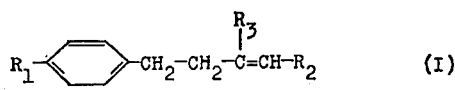

wherein $R_1$ represents a phenyl, phenoxy, phenylthio or cyclohexyl radical which is optionally substituted by halogen, nitro, alkyl and/or alkoxy, or a phenyl or cyclohexyl radical which is bonded via an alkylene, alkyleneoxy or alkylenethio bridge member, $R_2$ represents cyano, carbamoyl, an alkoxycarbonyl, alkenyloxycarbonyl, alkinyloxycarbamoyl, alkylcarbamoyl or dialkylcarbamoyl radical, and $R_3$ represents hydrogen or alkyl.

By an alkylene, alkyleneoxy or alkylenethio bridge member is meant a straight-chain or branched radical containing from 1 to 4 carbon atoms, in particular a —$CH_2$—, —$CH_2$—$CH_2$—, —$CH_2$—O—, —$CH_2$—$CH_2$—O—, —$CH_2$—S—, —$CH_2$—$CH_2$—S—, —$CH_2$—$CH_2$—$CH_2$—, radical.

Alkyl and alkoxy radicals are lower radicals containing from 1 to 5 carbon atoms, for example methyl, ethyl, n-propyl, isopropyl, n-butyl, isobutyl, tert,butyl, n-pentyl, iso-amyl, methoxy, ethoxy, propoxy, isopropoxy, n-butoxy, n-pentoxy, isoamyloxy etc.

By halogen is meant fluorine, chlorine, bromine and iodine, but chiefly chlorine and bromine.

The alkenyloxy oe alkinyloxy moiety of an alkenyloxy- or alkinyloxycarbonyl radical contain from 3 to 6, preferably 3 to 4 carbon atoms.

Examples od such radicals include allyloxy-, methallyloxy-, crotyloxy- and propargyloxycarbonyl.

Particularly important compounds are those of the formula

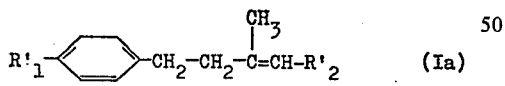

wherein $R'_1$ represents a phenoxy or phenylthio radical which is optionally substituted by $C_1$-$C_4$ alkyl and $R'_2$ represents methoxy-, ethoxy-, isopropoxy-, allyloxy-, propargyloxycarbonyl or diethylcarbamoyl.

The active substances of the formula I are manufactured in known manner by reacting a compound of the formula

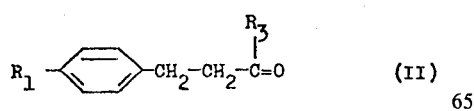

wherein $R_1$ and $R_3$ have the meanings given for formula I, with a phosphonic ester of the formula

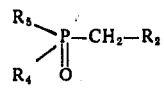

wherein $R_4$ and $R_5$ each represent $C_1$-$C_4$ alkoxy and $R_2$ has the meaning given for formula I, in the presence of a base.

Suitable bases are alcoholates, amides or hydroxides of alkali or alkaline earth metals, as well as strong basic amines.

The process is carried out in solvents and diluents which are inert towards the reactants, for example in aromatic hydrocarbons such as benzene, toluene, xylene, also alcohols such as methanol, ethanol, propanol, isopropanol or butanols, glycols; ethers, such as diisopropyl ether, tetrahydrofuran, dioxan or N,N-dialkylated amides, such as dialkylformamides; and N-methylpyrolidone, sulphoxides.

The reaction temperatures are in the range from 0°–150°C, but preferably from 20°–80°C.

The starting materials of the formula (II) can be manufactured, for example, by the process described in J.A. C.S. 80, 5524 ff (1958). In the manufacture of the compounds of the formula I, both possible geometric isomers are formed. The described compounds partly constitute mixtures of these isomers as occur during the synthesis.

In active substances of the formula I are suitable for combating plant hygiene and storage pests. In contrast to the majority of the hitherto known insecticides which in the form of contact or ingest poisons kill, paralyse or expel the pests, the active substances of the formula I influence their hormonal system.

Thus in the case of insects, for example, the shedding (in the case of hemimetabole) or the metamorphosis to the imago (in the case of holometabola), the laying of viable eggs and the development of deposited normal eggs is disturbed. The sequence of generations is interrupted and the pests are thus indirectly killed. The butene-carboxylic acid derivatives are virtually non-poisonous for warm blooded animals. Moreover, these compounds are easily decomposed so that a cumulation is impossible.

The new butene-carboxylic acid derivatives may be used primarily for combating the following plant, storage and hygiene pests:

| | |
|---|---|
| Orthoptera | Acrididae |
| | Gryllidae |
| | Blattidae |
| Isoptera | Kalotermitidae |
| Hemiptera | Miridae |
| | Piesmidae |
| | Lygaeidae |
| | Pyrrhocorodae |
| | Pentatomidae |
| | Cimicidae |
| | Reduviidae |
| | Jassidae |
| | Eriosomatidae |
| | Lecaniidae |
| | Aphididae |
| | Psyllidae |
| Coleoptera | Carabidae |
| | Elateridae |
| | Coccineffidae |
| | Tenebrionidae |
| | Dermestidae |
| | Cucujidae |
| | Chrysomelidae |
| | Curculionidae |
| | Scolytidae |
| | Scarabaeidae |

| Lepidoptera | -continued |
| --- | --- |
| | Pyralidae |
| | Phyticidae |
| | Pyraustidae |
| | Crambidae |
| | Tortricidae |
| | Galleriidae |
| | Lyonetiidae |
| | Yponomeutidae |
| | Pieridae |
| | Plutellidae |
| | Lymantriidae |
| | Noctuidae |
| Diptera | Culicidae |
| | Simuliidae |
| | Tipulidae |

The compounds of the formula I can be used as pure concentrate or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms
  dusts, tracking agents, granules, coated granules, impregnated granules and homogeneous granules.
Liquid forms:
  a. active substances which are dispersible in water: wettable powders, pastes, emulsions;
  b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal ets. These substances can either by used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk densitiy of 300 g/litre to 600 g/litre can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consists of active substance, carrier, optionally additives which stabilize the active substance, surface-active substances and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenyl and formaldehyde, as well as alkali, ammonium and alkaline earth metal salts of lignin sulfonic acid, in addition, alkylaryl sulfonates, alkali and alkaline earth metal salts of divutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are so mixed, ground, sieved and strained with the addtivies mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylene, toluene, dimethyl sulfoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substance or several active substances of general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1 to 95%, in which connection it should be mentioned that in the case of application from aircraft or some other suitable means of application, it is possible to use concentrations of up to 99.5% or even pure active substance.

The active substances of the formula I can, for example, be formulated as follows:

DUSTS

The following substances are used to manufacture (a) a 5% and (b) a 2% dust:

a.
 5 parts of active substance
 95 parts of talcum b.
 2 parts of active substance
 1 part of highly disperse silica
 97 parts of talcum, The active substances are mixed with the carriers and ground.

GRANULES

The following substances are used to manufacture 5% granules:
 5 parts of active substance
 0.25 part of epichlorohydrin
 0.25 part of cetyl polyglycol ether
 3.50 parts of polyethylene glycol
 91 parts of kaolin (particle size = 0.3–0.8 mm).

The active substance is mixed with epichlorohydrin and the mixture dissolved with 6 parts of acetone, then polyethylene glycol and cetyl polyglycol ether are added. The resulting solution is sprayed on kaolin and the acetone is subsequently evaporated in vacuo.

WETTABLE POWDER

The following constituents are used to manufacture a 10% wettable powder:

a.
 40 parts of active substance
 5 parts of sodium lignin sulphonate
 1 part of sodium dibutylnaphthalenesulphonic acid
 54 parts of silica;

b.
 25 parts of active substance
 4.5 parts of calcium lignin sulphonate
 1.9 parts of Champagne chalk/hydroxyethyl cellulose mixture (1:1)
 1.5 parts of sodium dibutylnaphthalenesulphonate
 19.5 parts of silica
 19.5 parts of Champagne chalk
 28.1 parts of kaolin;

c.
 25 parts of active substance
 2.5 parts of isooctylphenoxy-polyoxyethylene ethanol
 1.7 parts of Champagne chalk/hydroxyethyl cellulose mixture (1:1
 8.3 parts of sodium aluminium silicate
 16.5 parts of silica
 46 parts of kaolin;

d.
 10 parts of active substance
 3 parts of mixture of sodium salt of saturated fatty alcohol sulphates
 5 parts of naphthalenesulphonic acid formaldehyde condensate
 82 parts of kaolin.

The active substances are intimately mixed in appropriate mixing device with the adjuvants and ground in corresponding mills and rollers. Wettable powder are obtained which can be diluted with water to suspensions of every desired concentration.

EMULSIFIABLE CONCENTRATES

The following substances are used to manufacture (a) a 10% and (b) a 25% emulsifiable concentrate;

a.
 10 parts of active substance
 3.4 parts od epoxidised vegetable oil
 13.4 parts of a combination emulsifier consisting of fatty alcohol polyglycol ether and calcium alkylarylsulphonate
 40 parts of dimethyl formamide
 43.2 parts of xylene;

b.
 25 parts of active substance
 2.5 parts of epoxidised vegetable oil
 10 parts of an alkylarylsulphonate/fatty alcohol polyglycol ether mixture
 5 parts of dimethyl formamide
 57.5 parts of xylene.

Emulsion of every desired concentration can be manufactured by diluting these concentrates with water.

SPRAYS

The following constituents are used to manufacture a 5% spray:
 5 parts of active substance
 1 part of epichlorohydrin
 94 parts of petroleum ether(boiling limits: 160°–190°C).

This solution is sprayed using pressure sprays.

The agents described herein may be mixed with other biocidal active substances or agents. Besides the cited compounds of the general formula I, the new agents may thus contain, for example, insecticides, fungicides, bactericides, fungistatic agents, bacteriostatic agents, nematocides or herbicides, in order to broaden the activity spectrum.

EXAMPLE 1

1.1 While stirring, hydrogen chloride is passed for 16 hours at 90°C into a mixture of 816 g of diphenyl ether, 3,5 kg of concentrated hydrochloric acid and 520 g of 36% formaldehyde solution. The solution is then poured into ice water and extracted with diethyl ether/petroleum ether mixture. The organic phase is washed several times with water, dried over sodium sulphate with the addition of a small amount of potassium carbonate and evaporated. The residue is distilled in vacuo with the addition of potassium carbonate. Pure phenoxybenzyl chloride passes over at 143°–156°C/2 mm.

1.21 16 Grams of sodium are dissolved in 400 ml of absolute ethanol. Within 1 hour 182 g of ethyl acetoacetate are added dropwise to the still hot solution and then 156 g of phenoxybenzyl chloride are added at boiling temperature over the course of 3 hours. The mixture is boiled under reflux for a further 15 hours, cooled, the white precipitate which has formed filtered off and the solution evaporated. 100 Grams of sodium hydroxide in 2 litres of water are added to the residue and the mixture is stirred for 15 hours under reflux. It is then extracted with diethyl ether and the organic phases are dried and evaporated. The residue is distilled in a high vacuum to yield 4-(4'-phenoxy-phenyl)-2-butanone which boils at 144.5°–148°C/0.03 mm.

1.22 34 Grams of diphenyl ether dissolved in 100 ml of dry methylene chloride are added dropwise at 10°–20°C to a suspension of 35 g of anhydrous aluminium chloride in 100 ml of dry methylene chloride. Within 30 minutes, 14 g of methylvinyl ketone in 50 ml of methylene chloride are added to the mixture while cooling from time to time at 15°–20°C. The reaction suspension is then stirred for 2½ hours at 5°–10°C and subsequently poured on 1 litre of ice water. After the suspension has been strongly acidified with concentrated hydrochloric acid, the methylene chloride solution is isolated and the residual aqueous suspension extracted with 3 × 100 ml of methylene chloride. The combined methylene chloride extracts are washed until neutral with 3 × 400 ml of water, dried with sodium sulphate and filtered off. The methylene chloride is distilled off to leave 46.3 g of a green oil, which is fractionated in a high vacuum, yielding 23 g of 4-(4'-phenoxyphenyl)-2-butanone with a boiling point of 135-136°C at 0.001 Torr; $n_D^{20}$=1.5648.

1.3 30 Grams of dimethoxy-phosphinyl methyl acetate are slowly added dropwise at room temperature to a mixture of 24 g of 4-(4'-phenoxy-phenyl)-2-butanone, 7.2 g of approx. 50% sodium hydride and 750 ml of absolute benzene. A grey gelatinous substance forms which is stirred for a further 15 hours. Then 500 ml of purest dimethyl formamide are added and stirring is continued again for 5 hours. The mixture is then poured into water and extracted with diethyl ether. The organic phase is washed repeatedly with water, dried over sodium sulphate and evaporated. The residue is chromatographed on about 300 g of silica gel using benzene as eluant, to yield a cis-trans mixture of the compound of the formula

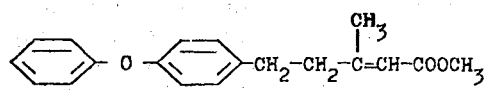

After repeated chromatography with silica gel and using benzene/petroleum ether (1:1) as eluant, about ⅓ pure cis-compound and ⅔ pure trans-compound are obtained.

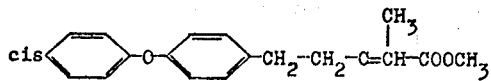

b.p.: 140°–150°C/0,001 Torr

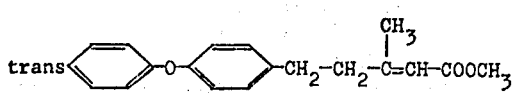

$N_D^{20}$ = 1,5638

The following compounds are manufactured analogously:

| Active Substance | Physical Data |
|---|---|
| 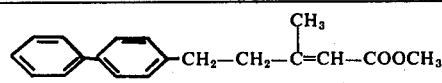 | $n_D^{20}$ = 1,5782 |
| 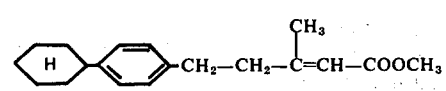 | $n_D^{20}$ = 1,5295 |
| 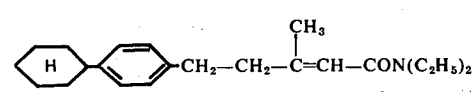 | $n_D^{20}$ = 1,5250 |
| 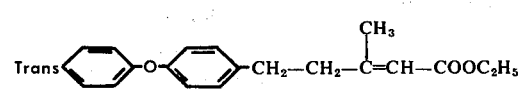 | $n_D^{20}$ = 1,5563 |
|  | b.p.:160–170°C/ 0,001 Torr |
| 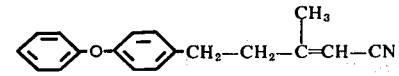 | $n_D^{20}$ = 1,5737 |
| 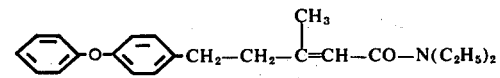 | $n_D^{20}$ = 1.5600 |
| 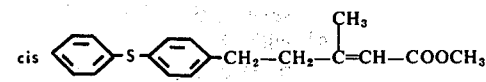 | $n_D^{20}$ = 1,5870 |

| Active Substance | Physical Data |
|---|---|
| trans ⟨C6H4⟩-S-⟨C6H4⟩-CH2-CH2-C(CH3)=CH-COOCH3 | $n_D^{20} = 1{,}5918$ |
| ⟨C6H5⟩-S-⟨C6H4⟩-CH2-CH2-C(CH3)=CH-C≡N | $n_D^{20} = 1{,}6081$ |
| trans ⟨C6H5⟩-S-⟨C6H4⟩-CH2-CH2-C(CH3)=CH-CO-N(C2H5)2 | $n_D^{20} = 1{,}5586$ |
| trans ⟨C6H5⟩-CH2-⟨C6H4⟩-CH2-CH2-C(CH3)=CH-COOCH3 | $n_D^{20} = 1{,}5587$ |
| ⟨C6H5⟩-CH2-⟨C6H4⟩-CH2-CH2-C(CH3)=CH-C≡N | $n_D^{20} = 1{,}5738$ |
| ⟨H-C6H10⟩-CH2-⟨C6H4⟩-CH2-CH2-C(CH3)=CH-COOCH3 | $n_D^{20} = 1{,}5252$ |
| trans Br-⟨C6H4⟩-O-⟨C6H4⟩-CH2-CH2-C(CH3)=CH-COOCH3 | $n_D^{20} = 1{,}5804$ |
| trans Br-⟨C6H4⟩-O-⟨C6H4⟩-CH2-CH2-C(CH3)=CH-C≡N | Sdp.: 91–93°C |
| Br-⟨C6H4⟩-O-⟨C6H4⟩-CH2-CH2-C(CH3)=CH-CO-N(C2H5)2 | $n_D^{20} = 1{,}5705$ |
| cis - C2H5-⟨C6H4⟩-O-⟨C6H4⟩-CH2-CH2-C(CH3)=CH-COOCH3 | $n_D^{20} = 1{,}5528$ |
| trans C2H5-⟨C6H4⟩-O-⟨C6H4⟩-CH2-CH2-C(CH3)=CH-COOCH3 | $n_D^{20} = 1{,}5550$ |
| C2H5-⟨C6H4⟩-O-⟨C6H4⟩-CH2-CH2-C(CH3)=CH-C≡N | $n_D^{20} = 1{,}5642$ |
| trans C2H5-⟨C6H4⟩-O-⟨C6H4⟩-CH2-CH2-C(CH3)=CH-CO-N(C2H5)2 | $n_D^{20} = 1{,}5196$ |
| ⟨C6H5⟩-CH2-O-⟨C6H4⟩-CH2-CH2-C(CH3)=CH-COOCH3 | $n_D^{20} = 1{,}5632$ |
| ⟨C6H5⟩-(CH2)2-O-⟨C6H4⟩-CH2-CH2-C(CH3)=CH-COOCH3 | $n_D^{20} = 1{,}5573$ |
| ⟨C6H5⟩-O-⟨C6H4⟩-CH2-CH2-C(CH3)=CH-COOC3H7(n)<br>Cis: trans = 5:4 | b.p.: 140–150°C/<br>0,001 Torr |
| ⟨C6H5⟩-O-⟨C6H4⟩-CH2-CH2-C(CH3)=CH-COOC3H7(i)<br>Cis: trans = 3:2 | b.p.: 140–150°C/<br>0,001 Torr |
| ⟨C6H5⟩-O-⟨C6H4⟩-CH2-CH2-C(CH3)=CH-COOC4H9(n)<br>Cis: trans = 3:2 | b.p.: 160–170°C/<br>0,001 Torr |

-continued
| Active Substance | Physical Data |
|---|---|
| 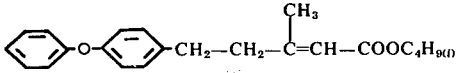 Cis: trans = 3:2 | b.p.:160–170°C/ 0,001 Torr |
| 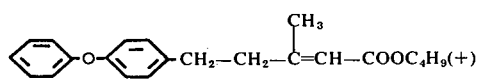 CH: trans = 3:2 | b.p.:155–162°C/ 0,001 Torr |
|  | $n_D^{20} = 1,5266$ |
| 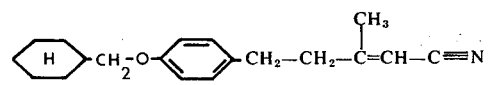 | $n_D^{20} = 1,5342$ |
|  | $n_D^{20} = 1,5282$ |
| 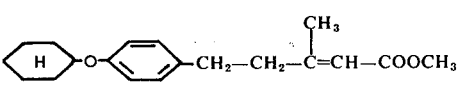 | $n_D^{20} = 1,5292$ |
| 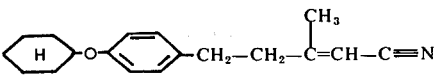 | $n_D^{20} = 1,5392$ |
| 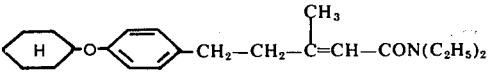 | $n_D^{20} = 1,5320$ |
| 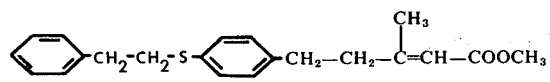 | $n_D^{20} = 1,5803$ |
|  | $n_D^{20} = 1,5761$ |
| 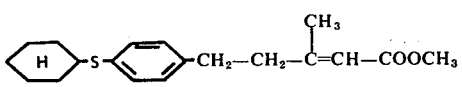 | $n_D^{20} = 1,5555$ |
|  | $n_D^{20} = 1,5548$ |
| 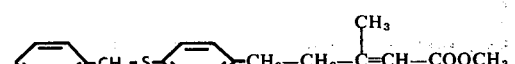 | $n_D^{20} = 1,5883$ |
| 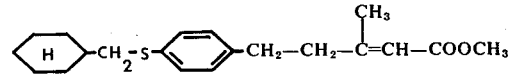 | $n_D^{20} = 1,5523$ |
| 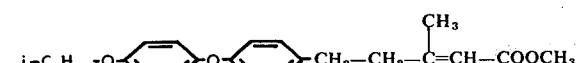 | $n_D^{20} = 1,5475$ |
|  | $n_D^{20} = 1,5497$ |
| 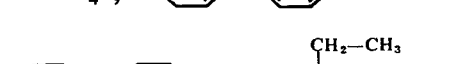 | b.p.:167°C/ 0,001 Torr |
|  | b.p.:168–174°C/ 0,0005 Torr |

-continued

| Active Substance | Physical Data |
|---|---|
| 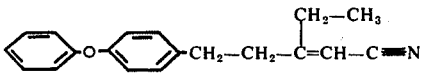 | b.p.:174–178°C/ 0,001 Torr |
| 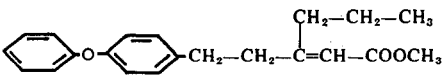 | $n_D^{20} = 1,5483$ |
| 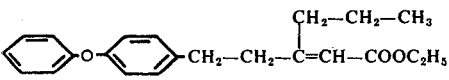 | $n_D^{20} = 1,5427$ |
| 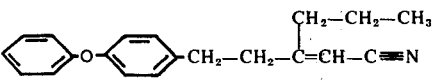 | $n_D^{20} = 1,5609$ |
| 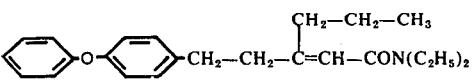 | $n_D^{20} = 1,5433$ |
| 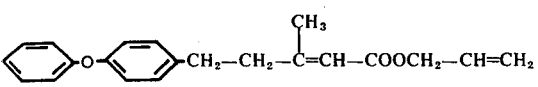 | |
| 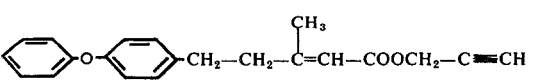 | |
| 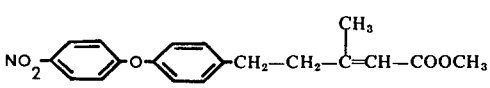 | b.p.:80°C |
| 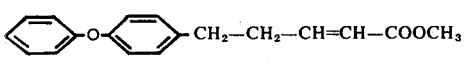 | |
| 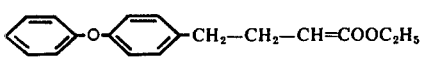 | |

EXAMPLE 2 a. Action against Dysdercus fasciatus

10 Dysdercus fasciatus larvae were treated topically with a solution of active substance in acetone in a concentration of 5γ 8 to 10 days before they are due to shed and emerge to the adult stage. The larvae were then kept at 28°C and 80–90% relative humidity. They were fed with meal made from pre-moistened cotton seeds.

After about 10 days, i.e. as soon as the controls had shed and emerged fully to the adult stage, the test subject were examined. Next to normal adults and dead larvae or pupae, special forms such as "super larvae" (larvae in which additional shedding occurs) and "adultoids" (adults with larval features) were found. The special forms are nonviable development stages which are not found in the normal development cycle.

The following table lists the number of normal animals which were found at the indicated concentration. No normal adults denotes 100% hormonal action.

| Active Substance | No. of Normal Adults |
|---|---|
| 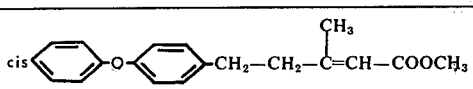 | 2 |
| 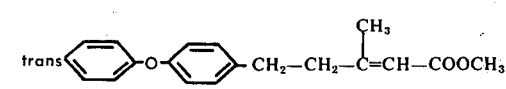 | 0 |
| 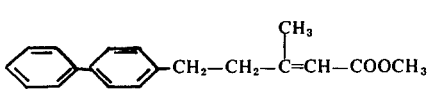 | 2 |
| 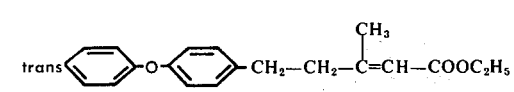 | 0 |

-continued
| Active Substance | No. of Normal Adults |
|---|---|
| cis 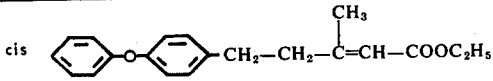 | 0 |
| 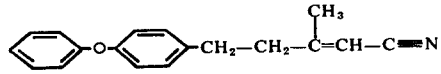 | 0 |
| 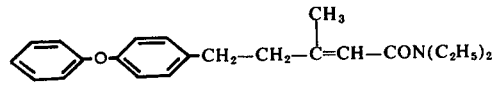 | 0 |
| trans 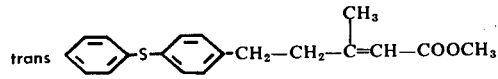 | 0 |
| 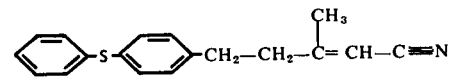 | 0 |
| 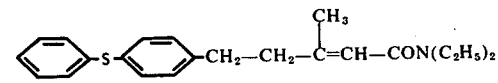 | 0 |
| trans 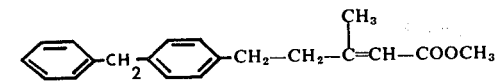 | 0 |
| 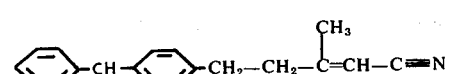 | 0 |
| 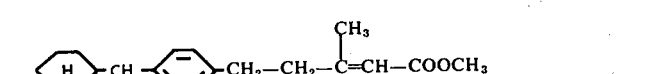 | 0 |
| trans 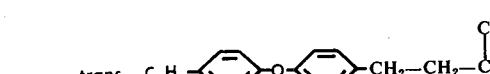 | 2 |
| 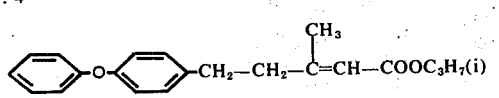 | 0 |
| cis:trans= 5 : 4  | 0 |
| cis:trans= 3 : 2 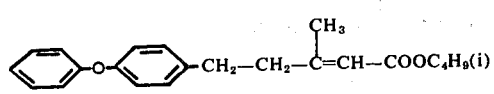 | 0 |
| cis:trans= 3 : 2  | 0 |
| cis:trans= 3 : 2 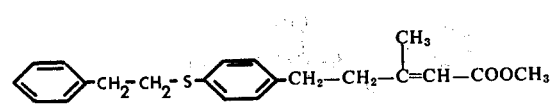 | 0 |
| cis:trans= 3 : 2 | 0 |

-continued

| Active Substance | No. of Normal Adults |
|---|---|
| C6H11-S-C6H4-CH2-CH2-C(CH3)=CH-COOCH3 | 0 |
| C6H5-CH2-S-C6H4-CH2-CH2-C(CH3)=CH-COOCH3 | 0 |
| C6H11-CH2-S-C6H4-CH2-CH2-C(CH3)=CH-COOCH3 | 0 |
| C6H5-O-C6H4-CH2-CH2-C(CH2CH3)=CH-COOCH3 | 0 |
| C6H5-O-C6H4-CH2-CH2-C(CH2CH3)=CH-COOC2H5 | 0 |
| C6H5-O-C6H4-CH2-CH2-C(CH2CH3)=CH-C≡N | 0 | b. Action against Dermestes spp.

10 Dermestes spp. pupae which had just shed were treated topically with a solution of active substance in acetonic in a concentration of 5γ. The test subjects were then kept at 28°C and 80–90% relative humidity.

The following table lists the number of normal animals which were found at the indicated concentration. No normal adults denotes 100% hormonal action.

| Active Substance | No. of Normal Adults |
|---|---|
| trans C6H5-O-C6H4-CH2-CH2-C(CH3)=CH-COOCH3 | 0 |
| trans C6H5-O-C6H4-CH2-CH2-C(CH3)=CH-COOC2H5 | 1 |
| cis C6H5-O-C6H4-CH2-CH2-C(CH3)=CH-COOC2H5 | 0 |
| C6H5-O-C6H4-CH2-CH2-C(CH3)=CH-CON(C2H5)2 | 0 |
| trans C6H5-S-C6H4-CH2-CH2-C(CH3)=CH-COOCH3 | 0 |
| C6H5-S-C6H4-CH2-CH2-C(CH3)=CH-CON(C2H5)2 | 0 |
| trans C6H5-CH2-C6H4-CH2-CH2-C(CH3)=CH-COOCH3 | 2 |
| C6H11-CH2-C6H4-CH2-CH2-C(CH3)=CH-COOCH3 | 0 |
| Br-C6H4-O-C6H4-CH2-CH2-C(CH3)=CH-COOCH3 trans | 2 |

| Active Substance | No. of Normal Adults |
|---|---|
| 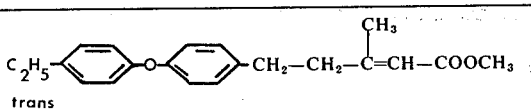 trans | 1 |
| 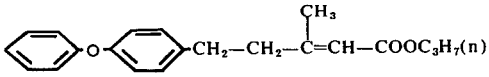 cis:trans= 5 : 4 | 0 |
| 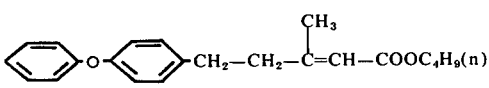 cis:trans= 3 : 2 | 0 |
|  cis:trans= 3 : 2 | 0 |
|  | 1 |
| 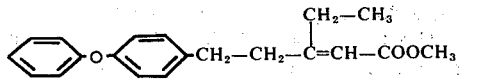 | 0 |
| 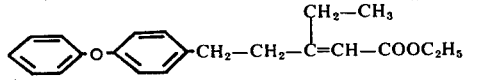 | 0 |
| 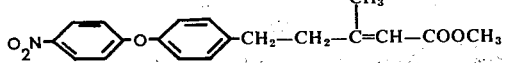 | 0 |

We claim:

1. An insecticidal composition comprising an insecticidally effective amount of a compound of the formula

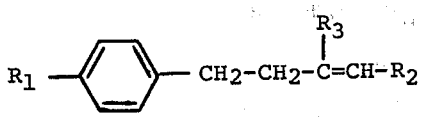

wherein $R_1$ represents a phenyl, phenoxy, phenylthio or cyclohexyl radical which is optionally substituted by halogen, nitro, $C_1$–$C_5$ alkyl or $C_1$–$C_5$ alkoxy, or a phenyl or cyclohexyl radical which is bonded via a $C_1$–$C_4$ alkylene, $C_1$–$C_4$ alkyleneoxy or $C_1$–$C_4$ alkylenethio bridge member, $R_2$ represents a ($C_1$–$C_5$ alkoxy) carbonyl, ($C_3$–$C_6$ alkenyloxy)carbonyl or, ($C_3$–$C_6$ alkinyloxy)carbonyl, radical and $R_3$ represents hydrogen or $C_1$–$C_5$ alkyl; together with a suitable carrier therefor.

2. The composition of claim 1, wherein said compound corresponds to the formula

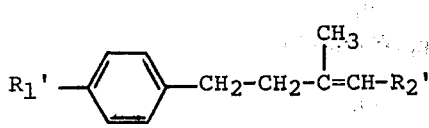

wherein $R_1'$ represents a phenoxy or phenylthio radical which is optionally substituted by $C_1$–$C_4$ alkyl and $R_2'$ represents methoxy-, ethoxy-, isopropoxy-, allyloxy-, or proparglyoxycarbonyl; together with a suitable carrier therefor.

3. The composition of claim 2, wherein said compound corresponds to the formula

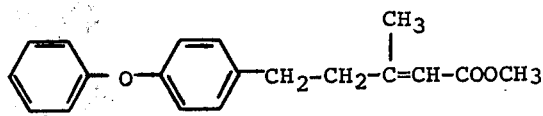

cis-trans-mixture

4. The composition of claim 2, wherein said compound corresponds to the formula

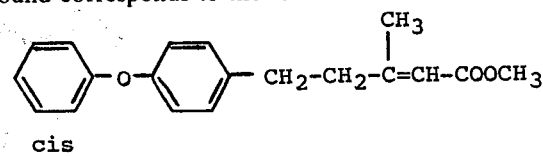

cis

5. The composition of claim 2, wherein said compound corresponds to the formula

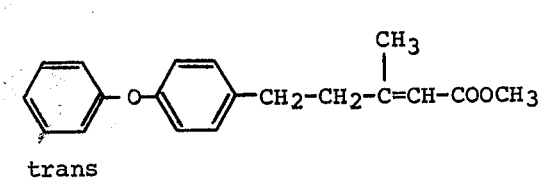

trans

6. The composition of claim 2, wherein said compound corresponds to the formula

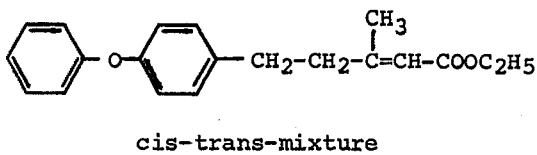

cis-trans-mixture

7. The composition of claim 2, wherein said compound corresponds to the formula

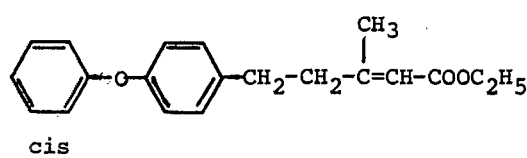

cis

8. The composition of claim 2, wherein said compound corresponds to the formula

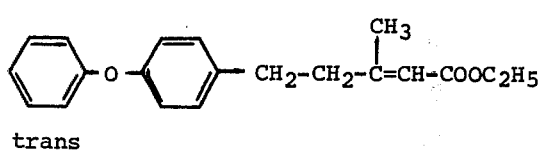

trans

9. The composition of claim 2, wherein said compound corresponds to the formula

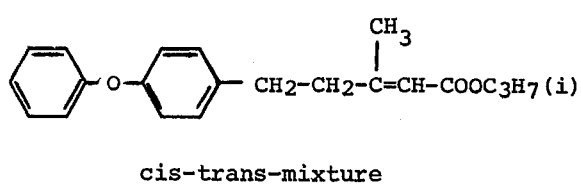

cis-trans-mixture

10. The composition of claim 2, wherein said compound corresponds to the formula

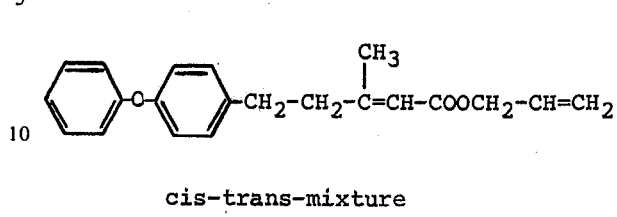

cis-trans-mixture

11. The composition of claim 2, wherein said compound corresponds to the formula

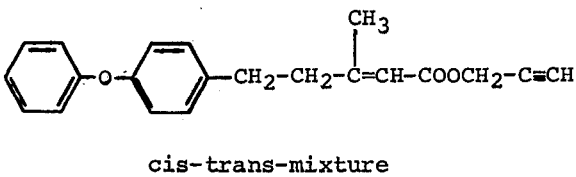

cis-trans-mixture

12. A method for combatting insects which comprises applying thereto an insecticidally effective amount of a compound of the formula of claim 1.

13. A method for combatting insects which comprises applying thereto an insecticidally effective amount of a compound which corresponds to the formula of claim 2.

* * * * *